(12) United States Patent
Broome et al.

(10) Patent No.: US 8,801,102 B2
(45) Date of Patent: Aug. 12, 2014

(54) TEST DEVICE FOR SEATING STRUCTURE

(75) Inventors: Mark Allen Broome, Holland, MI (US);
Matthew Reed, Ann Arbor, MI (US);
Timothy Hoogland, Holland, MI (US);
Douglas Woodard, Holland, MI (US)

(73) Assignee: Herman Miller, Inc., Zeeland, MI (US)

( * ) Notice: Subject to any disclaimer, the term of this patent is extended or adjusted under 35 U.S.C. 154(b) by 393 days.

(21) Appl. No.: 13/192,185

(22) Filed: Jul. 27, 2011

(65) Prior Publication Data

US 2012/0024079 A1 Feb. 2, 2012

Related U.S. Application Data

(60) Provisional application No. 61/369,415, filed on Jul. 30, 2010.

(51) Int. Cl.
*G01N 19/00* (2006.01)
*B60N 2/02* (2006.01)
*B60N 2/00* (2006.01)

(52) U.S. Cl.
USPC ....... 297/354.1; 297/353; 73/865.3; 73/865.9

(58) Field of Classification Search
USPC ............... 297/311, 440.11, 337, 353, 354.11, 297/354.1; 73/866.4, 865.3, 865.9
See application file for complete search history.

(56) References Cited

U.S. PATENT DOCUMENTS

| | | |
|---|---|---|
| 3,147,617 A | 9/1964 | Kaptur, Jr. et al. |
| 3,592,041 A | 7/1971 | Spencer |
| 3,753,302 A | 8/1973 | Daniel |
| 4,409,835 A | 10/1983 | Daniel et al. |
| 4,787,676 A * | 11/1988 | Neve de Mevergnies .... 297/353 |

(Continued)

FOREIGN PATENT DOCUMENTS

| | | |
|---|---|---|
| FR | 2927193 A1 | 8/2009 |
| GB | 986093 A | 3/1965 |

(Continued)

OTHER PUBLICATIONS

Eckelman et al. "Performance Test Method for Intensive Use Chairs—FNEW 83-269: A Description of the Test Method with Drawings". Purdue University Forestry and Natural Resources. Furniture Manufacturing. Sep. 2001. <http://www.extension.purdue.edu/extmedia/FNR/FNR-179.pdf>.*

(Continued)

*Primary Examiner* — Lisa Caputo
*Assistant Examiner* — Jonathan Dunlap
(74) *Attorney, Agent, or Firm* — Brinks Gilson & Lione

(57) ABSTRACT

A method of testing a seating structure includes disposing a seat engaging member on a seat and engaging a backrest material with an anthropometric surface of a back engaging member. The back engaging member is pivotally attached to the seat engaging member. A test device kit includes a plurality of seat engaging members having different flexibilities and a plurality of back engaging members having different anthropometric rear surfaces. Each of the back engaging members is pivotally connectable with each of the plurality of seat engaging members. A method of assembling a test device includes selecting a seat engaging member from a plurality of seat engaging members having different flexibilities and selecting a back engaging member having an anthropometric rear surface from a plurality of back engaging members each having a different anthropometric rear surface, and pivotally connecting the seat engaging member with the back engaging member.

25 Claims, 4 Drawing Sheets

(56) References Cited

U.S. PATENT DOCUMENTS

| | | | |
|---|---|---|---|
| 5,060,174 | A | 10/1991 | Gross |
| 5,373,749 | A | 12/1994 | Strand et al. |
| 5,379,646 | A | 1/1995 | Andrzejak et al. |
| 5,456,019 | A | 10/1995 | Dowell et al. |
| 5,641,917 | A | 6/1997 | Hurite et al. |
| 5,703,303 | A | 12/1997 | Stewart |
| 5,753,834 | A | 5/1998 | Stewart |
| 5,821,415 | A | 10/1998 | Faust et al. |
| 5,877,436 | A | 3/1999 | Faust et al. |
| 6,009,750 | A | 1/2000 | Maurer et al. |
| 6,116,102 | A | 9/2000 | Faust et al. |
| 6,131,436 | A | 10/2000 | O'Bannon et al. |
| 6,206,703 | B1 | 3/2001 | O'Bannon |
| 6,220,089 | B1 | 4/2001 | Gu et al. |
| 6,386,054 | B1 | 5/2002 | Jones et al. |
| 7,047,831 | B2 | 5/2006 | Reynolds et al. |
| 2003/0073552 | A1 | 4/2003 | Knight |
| 2004/0118229 | A1* | 6/2004 | Reynolds et al. ............ 73/866.4 |
| 2005/0091817 | A1 | 5/2005 | Eger et al. |
| 2005/0248202 | A1* | 11/2005 | Zheng ..................... 297/440.11 |
| 2006/0150756 | A1 | 7/2006 | Kassing et al. |
| 2007/0131043 | A1 | 6/2007 | Frost |
| 2008/0098831 | A1 | 5/2008 | Didyk et al. |
| 2008/0236308 | A1 | 10/2008 | Liebelt et al. |
| 2009/0025492 | A1 | 1/2009 | Hwang et al. |
| 2009/0151444 | A1 | 6/2009 | Kim et al. |
| 2010/0122415 | A1* | 5/2010 | Turner et al. ...................... 5/618 |
| 2010/0164266 | A1* | 7/2010 | Walters et al. ................ 297/337 |
| 2010/0289310 | A1* | 11/2010 | Huttenhuis ................... 297/311 |

FOREIGN PATENT DOCUMENTS

| | | |
|---|---|---|
| JP | 2002-350292 A | 12/2002 |
| JP | 2005-261508 A | 9/2005 |
| JP | 2007-290219 A | 11/2007 |
| WO | WO 99/19708 A1 | 4/1999 |
| WO | WO 2005/060794 A1 | 7/2005 |
| WO | WO 2008/080852 A1 | 7/2008 |

OTHER PUBLICATIONS

Stumpf et al., The Anthropometrics of Fit—Ergonomic criteria for the design of the Aeron® chair, © 2007, Herman Miller Inc., 4 pages.

American National Standards Institute, ANSI/BIFMA X5.1-2002, Product Testing, 16 pages.

* cited by examiner

TEST DEVICE FOR SEATING STRUCTURE

This application claims the benefit of U.S. Provisional Patent Application No. 61/369,415, filed Jul. 30, 2010, the entire disclosure of which is hereby incorporated herein by reference.

FIELD OF THE INVENTION

The present invention relates generally to a test device, and in particular, to a test device for a seating structure, such as an office chair, together with methods of use and assembly of the test device.

BACKGROUND

Seating structures typically are tested to ensure compliance with various durability standards. For example, office chairs may be tested in accordance with various ANSI/BIFMA standards, including for example ANSI/BIFMA X5.1-2002 (e.g, backrest durability tests—cyclic I, II and III). The test devices prescribed in such standards, however, may be more suitable for one type of chair as compared with others. For example, a load applying device, which may include a bridging member, may be limited in height, thereby increasing the point loads applied to the backrest of the chair. While suitable for various seating structures having a uniformly rigid back structure, such devices may not provide as reliable results for seating structures having more flexible body support structures, such as a suspended fabric or polymeric materials. Indeed, the non-anthropometric load applying devices may have a tendency to rip or tear the suspension material after repeated cycles due to the configuration of the devices, such that the testing does not accurately reflect the true durability of the seating structure. Conversely, such devices may mask actual failures that occur in the field due to actual use applications.

In addition, it may difficult to accurately position the load applying device at the designated height, since the device is not linked or tied to the seating surface. Moreover, seating structures may be configured in different sizes to accommodate different user populations. A "one size fits all" load applying device may not optimally interface with differently configured seating structures.

SUMMARY

The present invention is defined by the following claims, and nothing in this section should be considered to be a limitation on those claims.

In one aspect, one embodiment of a method of testing a seating structure having a backrest and a seat includes disposing a seat engaging member on the seat and engaging the backrest with an anthropometric surface of a back engaging member. In various embodiments, the backrest may be formed as a flexible, suspended material, including various woven and polymeric materials. The back engaging member is pivotally attached to the seat engaging member about a pivot axis. The anthropometric surface includes an upper thoracic region having an outwardly convex contour taken along a longitudinally extending vertical plane and a lower lumbar region. The method further includes pulling rearwardly on the thoracic region of the back engaging member for a predetermined number of cycles and thereby pivoting the back engaging member relative to the seat engaging member while simultaneously pivoting or tilting the backrest relative to the seat for the predetermined number of cycles.

In another aspect, one embodiment of a test device kit includes a plurality of seat engaging members having different flexibilities and a plurality of back engaging members. Each of the back engaging members has a different anthropometric rear surface. Each of the back engaging members is pivotally connectable with each of the plurality of seat engaging members.

In yet another aspect, a method of assembling a test device includes selecting a first seat engaging member from a plurality of seat engaging members having different flexibilities and selecting a first back engaging member having a first anthropometric rear surface from a plurality of back engaging members each having a different anthropometric rear surface. The method further includes pivotally connecting the first seat engaging member with the first back engaging member.

The various embodiments of the methods of testing, the test device kits and the methods of assembling the test devices provide significant advantages over other such test devices and methods for the use and assembly thereof. For example and without limitation, the anthropometric surface of the back engaging member may provide an accurate, reliable interface with the backrest, such that the durability of the seating structure may be more accurately evaluated. For example and without limitation, the anthropometric surface may allow for a more accurate load distribution, which is particularly useful when evaluating seating structures with flexible backrest members, including without limitation suspended materials that may not be particularly suitable for absorbing and distributing point loads. However, it should be understood that the test device also is suitable for use with more conventional, foam covered seating structures. In any of the embodiments, the test device essentially distributes the back load in the same fashion as a human when leaning back in a seating structure. The test device thereby allows the seating structure to react in the same way that the seating structure would react under actual loading conditions. In this way, the user can more accurately evaluate the durability of the seating structure.

In addition, the modularity of the system allows the operator to provide a proper interface with seating structures configured in different sizes, and having different seats, including for example suspended materials or more rigidly supported foam structures. At the same time, the coupling of the back engaging member to the seat engaging member ensures that the load application is maintained at a uniformly designated height, and thereby eliminates any operator error in the positioning thereof. The system is also inexpensive and easily/quickly assembled and/or reconfigured.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

DETAILED DESCRIPTION OF THE PRESENTLY PREFERRED EMBODIMENTS

It should be understood that the term "plurality," as used herein, means two or more. The term "longitudinal," as used herein means of or relating to length or the lengthwise direction, and in general corresponds to a direction running between a front and back, for example from a front of a seat to a back thereof, or between a top and bottom, for example from a top of a backrest to a bottom thereof. The term "lateral," as used herein, means situated on, directed toward or running from side to side, for example from one side of a seat or backrest to the other side thereof. The terms "first," "second," and so on, as used herein also are not meant to be assigned to a particular component so designated, but rather are simply referring to such components in the numerical order as addressed, meaning that a component designated as "first" may later be a "second" such component, depending on the order in which it is referred. It should also be understood that designation of "first" and "second" does not necessarily mean that the two components or values so designated are different, meaning for example a first member may be the same as a second member, with each simply being applicable to different components. The term "suspended" as used herein means any flexible material that is put in tension between spaced apart support members. The term "coupled" means connected to or engaged with, whether directly or indirectly, for example with an intervening member, and does not require the engagement to be fixed or permanent, although it may be fixed or permanent, and includes both mechanical and electrical connection.

The phrases "anthropometric shape," "anthropometric surface," and derivations thereof, refer to shapes and surfaces approximating the human body based on data relating to the physical dimensions and proportions of the human body. For example and without limitation, the back engaging members 14a, 14b, 14c disclosed herein are configured with outer, rear anthropometric shapes based on the CAESAR 2002 Anthropometric data. It should be understood that the anthropometric shapes may be based on other data. In one embodiment, the anthropometrics range from a $5^{th}$ percentile female to a $95^{th}$ percentile male, and include within that range a $50^{th}$ percentile male.

Figure 1:
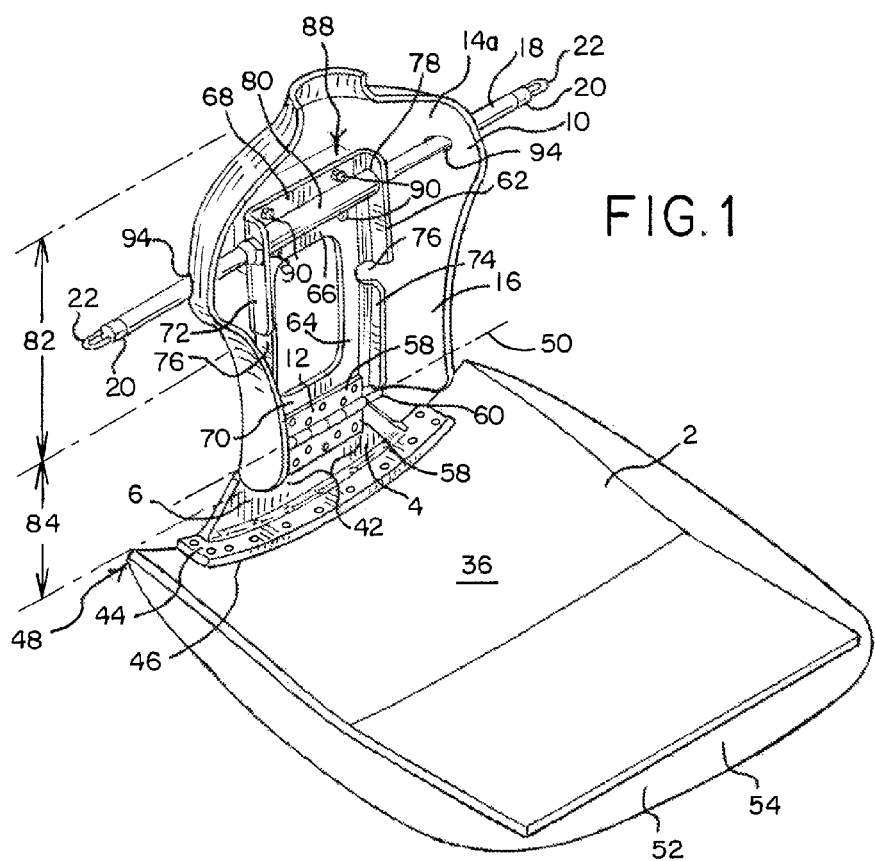
FIG. 1 is a perspective view of one embodiment of a test device.
Figure 4:
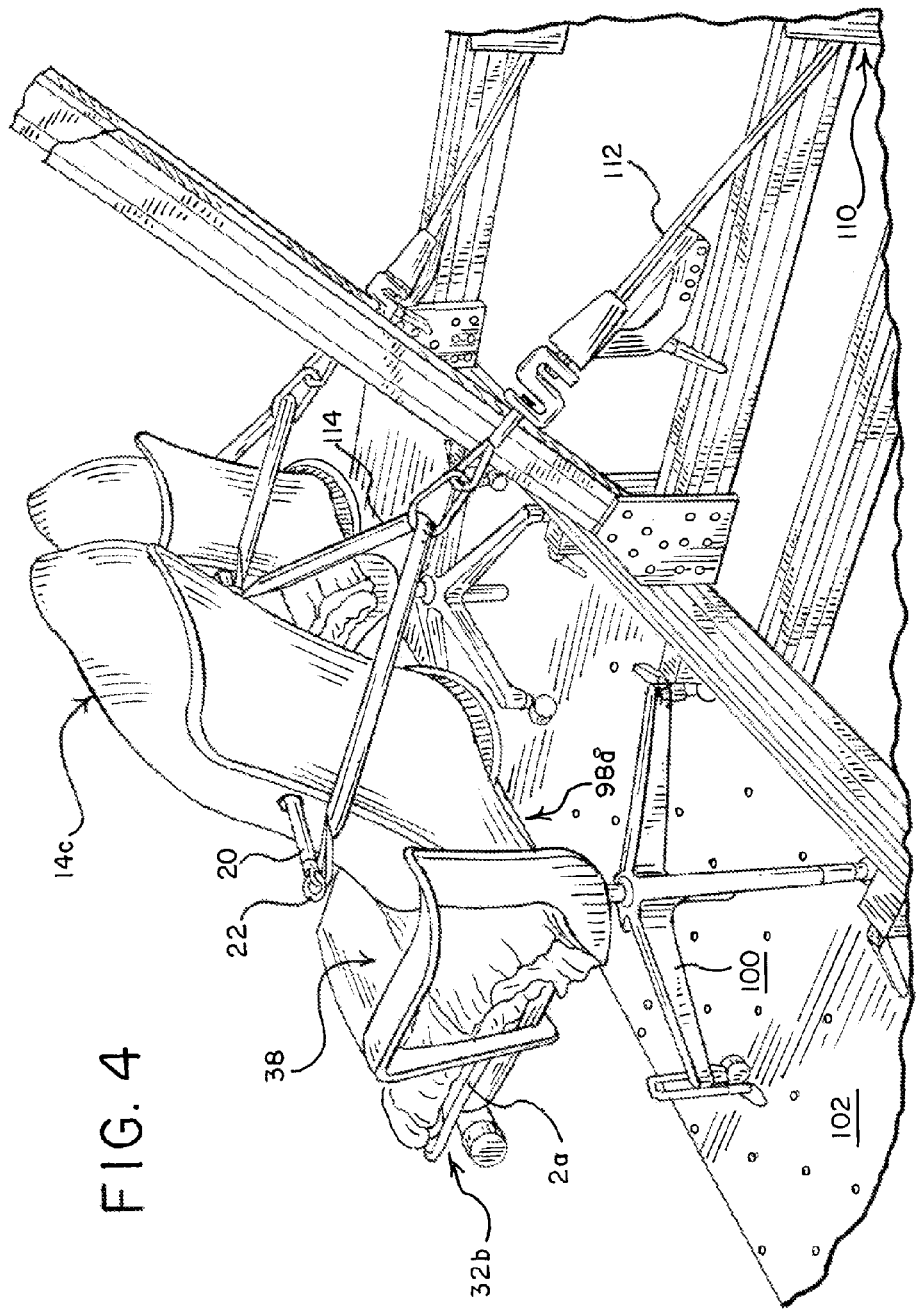
FIG. 4 is a rear perspective view of one embodiment of a test device applied to, and operating on, one embodiment of an office chair.
Figure 5:
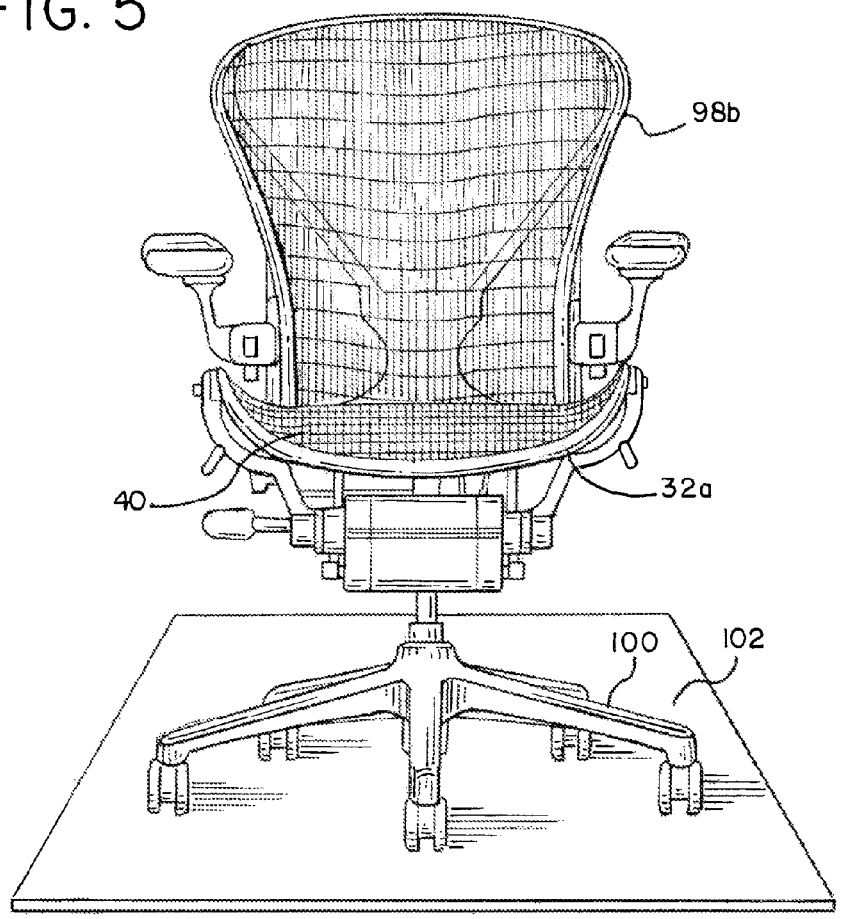
FIG. 5 is a front view of one embodiment of a chair with a suspended backrest material.

Referring to FIG. 1, a test device 30 includes a seat engaging member 2, 2a that is configured to be supported by a seat 32a, 32b, as disclosed for example in FIGS. 4 and 5. The seat engaging member 2, 2a may be made of different materials having different flexibilities or rigidity, including a rubber or plastic, and provides a platform to support auxiliary weights if needed, as shown in FIG. 4. The terms "flexible" and "flexibility" refer to a pliable material that is capable of being bent or displaced repeatedly without injury or damage. The stiffness, k, of a component is one measure of flexibility, and is defined by the measure of the resistance offered by an elastic body to deformation in response to an applied force along a given degree of freedom (DOF) when a set of loading points and boundary conditions are prescribed on the elastic body. It is an extensive material property, meaning it is a property of the structure, and is affected by the shape and boundary conditions of the component, together with the intensive properties thereof, such as elastic modulus. Both embodiments of the seat engaging member provide for a low cost, thin sheet of material having an enlarged flat upper surface 36, which is ideally suited for supporting auxiliary weights 38 in a stable manner that may approximate a user sitting on the chair.

Figure 2:
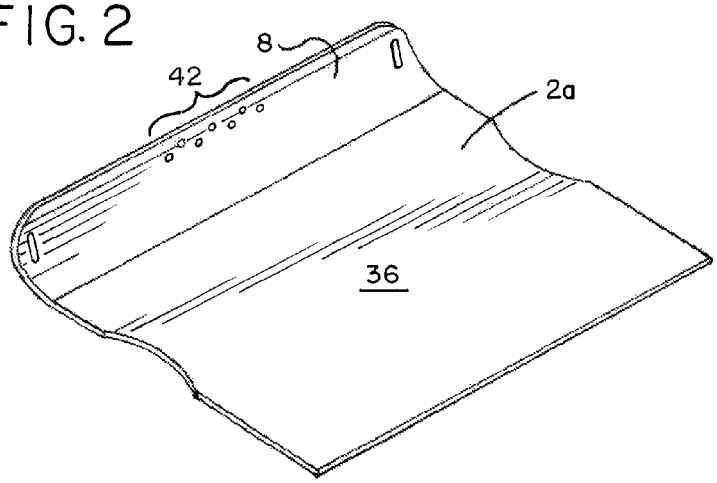
FIG. 2 is a perspective view of an alternative embodiment of a seat engaging member.

When engaging a more flexible seat surface 40, such as the suspended seat surface of the chair shown in FIG. 5, a more rigid material having a higher modulus of elasticity, such as 0.188 inch Delrin material may be used for the seat engaging member 2a as shown in FIG. 2. Conversely, when the seat is configured with a more rigid seat 52, such as a foam covered shell, a more flexible seat engaging member 2, such as a rubber material having a relatively lower modulus of elasticity, may be used such that it may more easily conform to the contour of the seating surface 54. However, it should be understood that the more flexible seat engaging member 2 may be used with a more flexible seat surface (e.g. suspended material), and the more rigid seat engaging member 2a may be used with a more rigid seat surface (e.g. foam covered shell).

In the first embodiment, the rear portion 8 of the seat engaging member 2a is configured as an upturned portion, which curves upwardly and rearwardly. A hole pattern 42 is provided in the upturned portion 8 and is configured to mate with one side of a universal hinge 12.

In the embodiment of FIG. 1, the seat engaging member includes a coupling 4 attached to a rear portion thereof. The coupling may be made of metal, such as aluminum, or any other suitable material, including various plastics, composites, wood, etc. The coupling has a vertical flange 6 that extends upwardly and includes a hole pattern 42 also configured to mate with the universal hinge. The coupling further includes a bottom flange 44 having a curved bottom surface 46, preferably with a radius of between about 18 and 24 inches, or about 20.8 inches in one embodiment, with the curved flange having a laterally extending width of about 15 inches. The bottom surface is secured to the seat engaging member 2, which conforms to the curve of the coupling and has a lower curved surface 48 formed along a rear portion thereof. The radius of the curved surface is preferably calculated so as to match, or approximate, the rear seating surface of various seating structures, including for example and without limitation the AERON "C" chair, the FORAY chair and the NALA chair, all available from Herman Miller, Inc., Zeeland, Mich. As such, the radius, or contour of the surface, may be altered to conform to other seating structures. In one embodiment, the radius also closely matches or approximates the radius of a 95% male at the iliotibial tract attachment points.

In either embodiment of the seat engaging member, the upturned portion 8 and/or the coupling 4 ensure that the position of the hinge 12, and in particular the pivot axis 50 thereof, is maintained at a predetermined height above the surface of the seat 40, 54. In particular, the hinge axis 50 is positioned at the CAESAR data 2002 50% composite male/female sacral pivot, which also is approximately midway between the 95% male and 5% female sacral pivots. In one embodiment, the hinge 12 is configured with opposite leaf members 58 joined with a pin 60.

Figure 6:
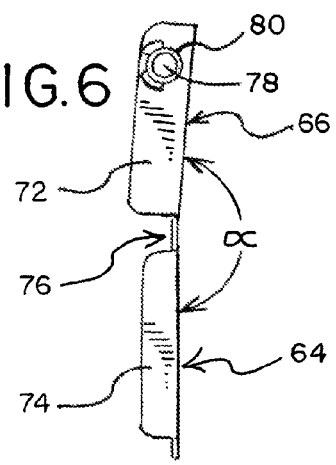
FIG. 6 is a side view of a support bracket.

Referring to FIGS. 1 and 6, a universal support bracket 62 includes a lower portion 64 and an upper portion 66 that function as a spine support for the back engaging member 14a, 14b, 14c. Each portion has a center web 68, 70 and a pair of side flanges 72, 74 that increase the bending strength and stability thereof. A bottom of the lower portion is configured with a hole pattern 42 that mates with the upper leaf member 58 of the hinge. The upper and lower portions 64, 66 are separated by cutouts 76 between the side flanges, which permit the rear surfaces of the lower and upper portions 64, 66 to be bent and angled relative to one another as shown in FIG. 6 at the angle "α." The side flanges of the upper portion have aligned openings 78 formed therethrough, and may be configured with bushings, or with a tube 80 that extends between the side flanges 72 and is attached thereto, for example by welding.

Figure 3:
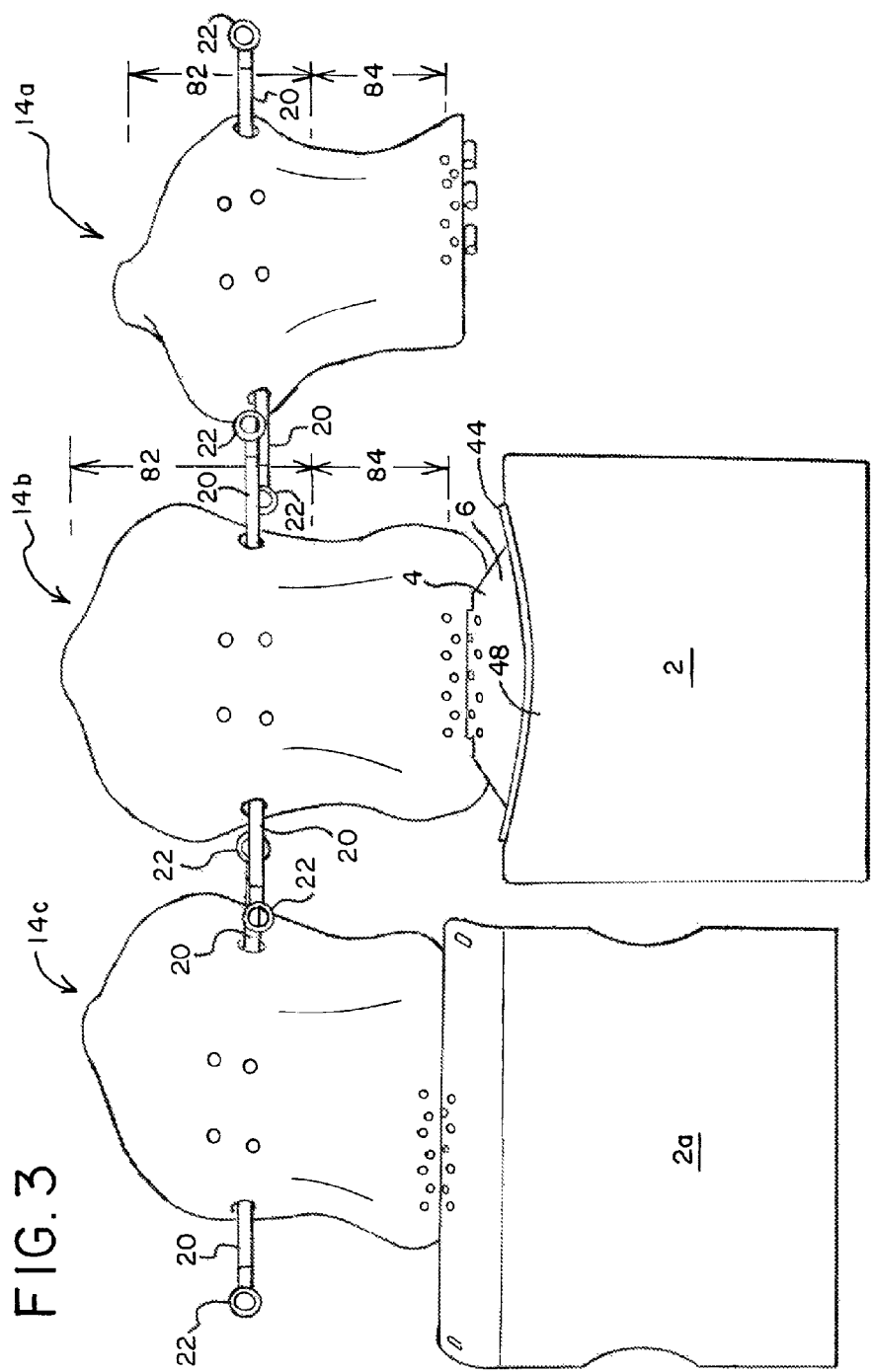
FIG. 3 is a plan view of three different embodiments of a back engaging member and two different embodiments of a seat engaging member.

Referring to FIGS. 1, 3 and 4, a plurality of back engaging members 14a, 14b, 14c are shown. In one embodiment, three back engaging members are configured with an outer, anthropometric surface approximating a 95% male 14c, 50% male 14b and a 5% female 14a respectively. Of course, other anthropometric shapes and sizes may be provided. Each of the back engaging members has an upper thoracic portion 82 and a lower lumbar portion 84, with the thoracic portion having an outwardly facing convex shape taken along a central vertical plane, and the lower lumbar portion having an outwardly facing concave shape taken along the central vertical plane. As shown, the upper thoracic portion 82 is wider than the lower lumbar portion 84 on each of the back engaging members. Each of the back engaging members is open to the front and defines a cavity 88. Of course, the back engaging members may also include a front. Preferably, in order to maintain the modularity of the system, each of the back engaging members is connectable to the universal support bracket 62, for example with a plurality of removable fasteners 90. In one embodiment, the upper portion 68 is secured in an interior of the thoracic portion of the back engaging member. Alternatively, the back engaging members may be attached to the support bracket with adhesive, or combinations of fasteners and adhesive. The back engaging members are preferably made of a rigid, plastic material with a smooth outer surface.

Referring to FIGS. 1, 3 and 4, a load input member 20, configured in one embodiment as a rod, is inserted through the tube portion 80 of the support bracket, and extends through aligned openings 94 formed in the sides of the back engaging member in the thoracic region thereof. The ends of the load input member are configured with loop members 22 that are rotatable about an axis of the rod. The height of the load input member is based on the ANSI/BIFMA X5.1-2002 standard, and is located about 16 inches above the seating surface in one embodiment in the thoracic region of the back engaging member.

The test device is modular, and may be configured as a kit including a plurality of differently configured seat engaging members 2, 2a, a plurality of differently configured back engaging members 14a, 14b, 14c, and a universal support bracket 62 configured with a load input member 20 and a hinge 12. For example and without limitation, in one embodiment, the kit may include a 95% male back engaging member 14c and a 5% female back engaging member 14a. The kit may include other back engaging members, such as a 50% male back engaging member 14b, or may include only a single back engaging member. The kit also may include only a single seat engaging member.

In operation, the user evaluates the seating structure to be tested and selects one of a plurality of seat engaging members 2, 2a based on the configuration of the seat. For example, the user may select a more rigid seat engaging member 2a if the seat is configured with a flexible suspended material that is not able to absorb point loads. Conversely, the user may select the less rigid seat engaging member 2 so as to conform the seat engaging member to a seat having a predefined contour. After selection, the seat engaging member is connected to the universal hinge 12.

The user also evaluates the backrest 98a, 98b and selects one of the back engaging members 14a, 14b, 14c. It should be understood that the present test device may be used with various flexible backrests, including various suspensions materials and frame supported polymeric materials, as well as more conventional foam covered backrests. During the course of testing, more than one back engaging member may be incorporated into the test device and applied to the same seating structure. The test device is quickly and easily reconfigured, without the need to remove or move the seat engaging member relative to the seating structure being evaluated, simply by removing the hinge pin, removing the first back engaging member and connecting a second, selected back engaging member with the hinge pin. The selected back engaging member 14a, 14b, 14c is connected to the support bracket 62, which is preferably configured with a hinge 12. The load input member 20 is inserted through the back engaging member and support bracket. Preferably, the load input member does not engage or apply a load directly to the back engaging member, but rather applies the load to the support bracket 62, which then distributes the load to the back engaging member.

In operation, the assembled test device is applied to a seating structure, as shown for example in FIG. 3 or 5. The seating structure, for example a base 100 thereof, may be secured to a platform 102. The seat engaging member is disposed or positioned on the seat 32a, 32b, 52, with the back engaging member disposed or positioned against the backrest member 98a, 98b. Auxiliary weights 38, for example 225 lbs, are applied to the top surface of the seat engaging member, for example and without limitation in accordance with ANSI/BIFMA X5.1-2002. A load input machine 110 is then connected to the test device. For example, in one embodiment, a pair of straps 114 is connected to the looped ends 22 of the load input member 20. The straps 114 are connected to a chain, cable or other load applicator 112, which in turn pulls the load input member 20 rearwardly a predetermined number of times. For example and without limitation, the load applicator 112 may apply a load of about 445 N (100 lbf.) to the load input member 20 at a rate of between 10 and 30 cycles per minute for a 120,000 cycles as set forth in ANSI/BIFMA X5.1-2002. Of course, different loads may be applied at different rates for different numbers of cycles. As the load input member is pulled rearwardly, the back engaging member 14a, 14b, 14c is pivoted relative to the seat engaging member 2, 2a, and the back 98a, 98b is simultaneously pivoted relative to the seat 32a, 32b, 52.

A complete cycle is defined as a rearward pivoting of the back engaging member 14a, 14b, 14c and back 98a, 98b from an initial position to a rearward tilt position, with a return forward pivoting of the back engaging member 14a, 14b, 14c and back 98a, 98b from the rear tilt position to the initial position. The return may be accomplished by easing the load applied to the back engaging member, with biasing springs or structure incorporated into the seating structure returning the back to the initial position. It should be understood that some seating structures provide linkages or hinges to allow for the pivoting of the backrest 98b relative to the seat 32a, while in other embodiments, the backrest 98a is pivotable or tiltable relative to the seat 32b by way of bending of frame members connecting the seat and backrest, with the present test device 10 equally applicable to both types of seating structures.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A method of testing a seating structure comprising:
   providing a seating structure comprising a seat and a backrest, wherein said backrest is tiltable relative to said seat;
   positioning a test device on said seating structure, including:
      disposing a seat engaging member on said seat;
      engaging said backrest with an anthropometric surface of a back engaging member, wherein said back engaging member is pivotally attached to said seat engaging member about a pivot axis, and wherein said anthropometric surface comprises an upper thoracic region and a lower lumbar region; and
   pulling rearwardly on said thoracic region of said back engaging member for a predetermined number of cycles and thereby pivoting said back engaging member relative to said seat engaging member and simultaneously tilting said backrest relative to said seat for said predetermined number of cycles.

2. The method of claim 1 wherein said backrest comprises a flexible, suspended backrest material.

3. The method of claim 2 wherein said suspended backrest material comprises a woven material.

4. The method of claim 2 wherein said suspended backrest material comprises a polymeric material.

5. The method of claim 1 wherein said back engaging member comprises a first back engaging member and said anthropometric shape comprises a first anthropometric shape, and further comprising removing said first back engaging member and pivotally attaching a second back engaging member having a second anthropometric shape to said seat engaging member, wherein said second anthropometric shape is different than said first anthropometric shape.

6. The method of claim 1 wherein said seat engaging member is pivotally attached to said back engaging member with a hinge member.

7. The method of claim 1 wherein a rear portion of said seat engaging member comprises a bottom convex curved surface taken along a laterally extending vertical plane.

8. The method of claim 1 wherein said seating structure comprises a first seating structure and wherein said seat engaging member comprises a first seat engaging member formed from a flexible material, and further comprising removing said first seat engaging member and connecting a second seat engaging member to said back engaging member, wherein said second seat engaging member is formed from a semi-rigid material having less flexibility than said first seat engaging member, and positioning said test device on a second seating structure.

9. The method of claim 1 wherein said pulling rearwardly on said thoracic region of said back engaging member for said predetermined number of cycles comprises pulling rearwardly on a load input member extending laterally through said back engaging member.

10. The method of claim 1 further comprising positioning an auxiliary weight on an upper surface of said seat engaging member.

11. The method of claim 1 wherein said pivot axis is positioned above an upper surface of said seat.

12. A test device kit comprising:
    at least one seat engaging member having a predetermined flexibility; and
    a plurality of back engaging members, each having a different anthropometric rear surface, wherein each of said back engaging members is pivotally connectable with said at least one seat engaging member.

13. The test device kit of claim 12, wherein said at least one seat engaging member comprises a plurality of seat engaging members having different flexibilities.

14. The test device kit of claim 13 further comprising a universal hinge connectable to each of said plurality of seat engaging members and connectable to each of said plurality of said back engaging members.

15. The test device kit of claim 14 wherein at least one of said seat engaging members comprises a coupling connectable to said universal hinge, wherein said coupling comprises a lower, laterally extending curved surface.

16. The test device kit of claim 12 wherein said plurality of back engaging members comprises at least a first back engaging member having a 95% male shaped rear surface and a second back engaging member having a 5% female shaped rear surface.

17. The test device kit of claim 16, wherein said 95% male shaped rear surface and said 5% female shaped rear surface are based on CAESAR 2002 Anthropometric data.

18. The test device kit of claim 16 wherein said plurality of back engaging members further comprises at least a third back engaging member having a 50% male rear surface.

19. A method of assembling a test device comprising:
    selecting a first back engaging member having a first anthropometric rear surface from a plurality of back engaging members each having a different anthropometric rear surface; and
    pivotally connecting a seat engaging member with said first back engaging member.

20. The method of claim 19 further comprising, selecting said seat engaging member from a plurality of seat engaging members having different flexibilities.

21. The method of claim 20 wherein said pivotally connecting said first seat engaging member with said first back engaging member comprises connecting said first seat engaging member to one side of a hinge member and connecting said first back engaging member to an opposite side of said hinge member.

22. The method of claim 21 wherein said seat engaging member comprises a coupling, wherein said connecting said seat engaging member to said one side of said hinge member comprises connecting said coupling to said one side of said hinge member, wherein said coupling comprises a lower, laterally extending curved surface.

23. The method of claim 19 wherein said first back engaging member has a 95% male shaped rear surface and wherein a second back engaging member comprises has a 5% female shaped rear surface.

24. The method of claim 23 wherein a third back engaging member has a 50% male rear surface.

25. The method of claim 23, wherein said 95% male shaped rear surface and said 5% female shaped rear surface are based on CAESAR 2002 Anthropometric data.

* * * * *